United States Patent

Nishitani et al.

Patent Number: 5,017,581
Date of Patent: May 21, 1991

[54] PYRIDONECARBOXYLIC ACIDS AND THEIR ANTI-BACTERIAL COMPOSITIONS

[75] Inventors: Yasuhiro Nishitani; Yutaka Nishino; Tadashi Irie, all of Osaka, Japan

[73] Assignee: Shionogi & Co., Ltd., Osaka, Japan

[21] Appl. No.: 413,679

[22] Filed: Sep. 28, 1989

[30] Foreign Application Priority Data

Oct. 3, 1988 [JP] Japan .................. 63-249659

[51] Int. Cl.$^5$ .................. A61K 31/47; C07D 215/54; C07D 471/04
[52] U.S. Cl. .................. 514/300; 514/312; 546/123; 546/156
[58] Field of Search ............ 546/123, 156; 544/300, 544/312

[56] References Cited

U.S. PATENT DOCUMENTS 4,786,649 11/1988 Ueda et al. .................. 546/156

*Primary Examiner*—Mary C. Lee
*Assistant Examiner*—Bernard I. Dentz

*Attorney, Agent, or Firm*—Wenderoth, Lind & Ponack

[57] ABSTRACT

A compound of the formula

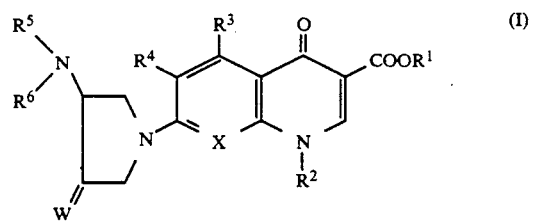

wherein $R^1$ is hydrogen or a protecting group; $R^2$ is $C_1$-$C_3$ alkyl or $C_3$-$C_7$ cycloalkyl; $R^3$ is hydrogen, hydroxy, or amino; $R^4$ is halogen; $R^5$ and $R^6$ each is identically or differently hydrogen or $C_1$-$C_3$ alkyl; W is $C_1$-$C_3$ alkylidene; X is N or C-Y; Y is hydrogen or halogen; or a pharmaceutically acceptable salt thereof, having a more potent antibacterial activity against G(+) and G(−) bacteria than known analogues, useful as antibacterial agents.

9 Claims, No Drawings

PYRIDONECARBOXYLIC ACIDS AND THEIR ANTI-BACTERIAL COMPOSITIONS

BACKGROUND OF THE INVENTION

1. Field of the Invention

The present invention relates to novel pyridonecarboxylic acids exhibiting excellent antibacterial activities against Gram-positive and Gram-negative bacteria.

2. Prior Art

Pyridonecarboxylic acids described in U.S. Pat. No. 4,382,892, U.S. Pat. No. 4,528,287, FR. Pat. No. 2,563,521, and EP Pat. No. 195,841 Specifications have been known as antibacterial agents. Many of these known products have problems such as induction of adverse effects like convulsions when administered to humans. Consequently, the aim of this invention is to supply pyridonecarboxylic acids having strong antibacterial activity, but reduced CNS actions such as convulsions.

SUMMARY OF THE INVENTION

This invention provides novel pyridonecarboxylic acids, comprising a pyrrolidine ring at the 7-position of the formula shown hereunder, being substituted by amino group and alkylidene group, which are particularly valuable as antibacterial agents for oral administration.

DETAILED DESCRIPTION

The present invention relates to compounds of the formula:

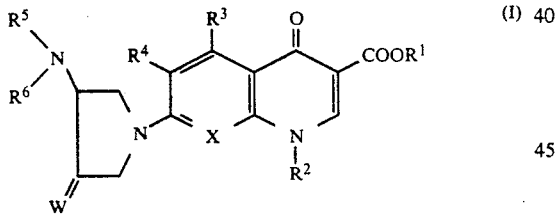

wherein $R^1$ is hydrogen or a protecting group; $R^2$ is $C_1$-$C_3$ alkyl or $C_3$-$C_7$ cycloalkyl; $R^3$ is hydrogen, hydroxy, or amino; $R^4$ is halogen; $R^5$ and $R^6$ each is identically or differently hydrogen or $C_1$-$C_3$ alkyl; W is $C_1$-$C_3$ alkylidene; X is N or C-Y; Y is hydrogen or halogen, or pharmaceutically acceptable salt thereof.

In this invention, $C_1$-$C_3$ alkyl means straight or branched chain $C_1$-$C_3$ alkyl, including methyl, ethyl, n-propyl, and isopropyl.

Halogen means chlorine, bromine, fluorine, or iodine.

Protecting group means all the known protecting group for carboxy, including, for example, $C_1$-$C_3$ alkyl, $C_3$-$C_7$ cycloalkyl, and benzyl.

$C_1$-$C_3$ alkylidene group means methylene, ethylidene, propylidene, or isopropylidene.

The compound (I) of this invention can be prepared by the following method.

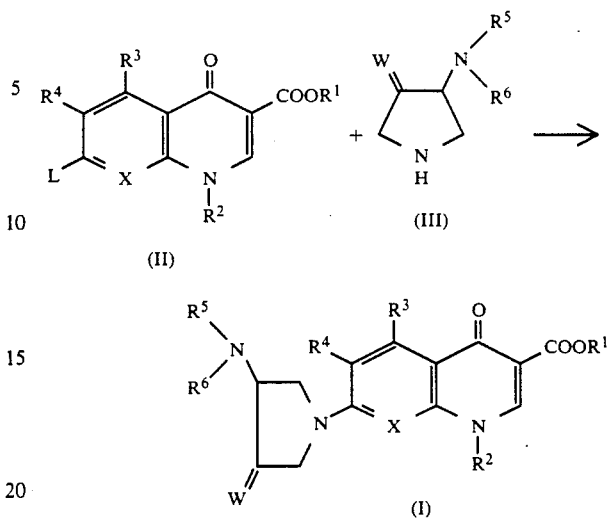

wherein L means leaving group, and $R^1$, $R^2$, $R^3$, $R^4$, $R^5$, $R^6$, W, and X have the same meanings as defined above.

The starting material (II) can be prepared according to the process as described in U.S. Pat. No. 4,382,892.

The reaction scheme is illustrated below.

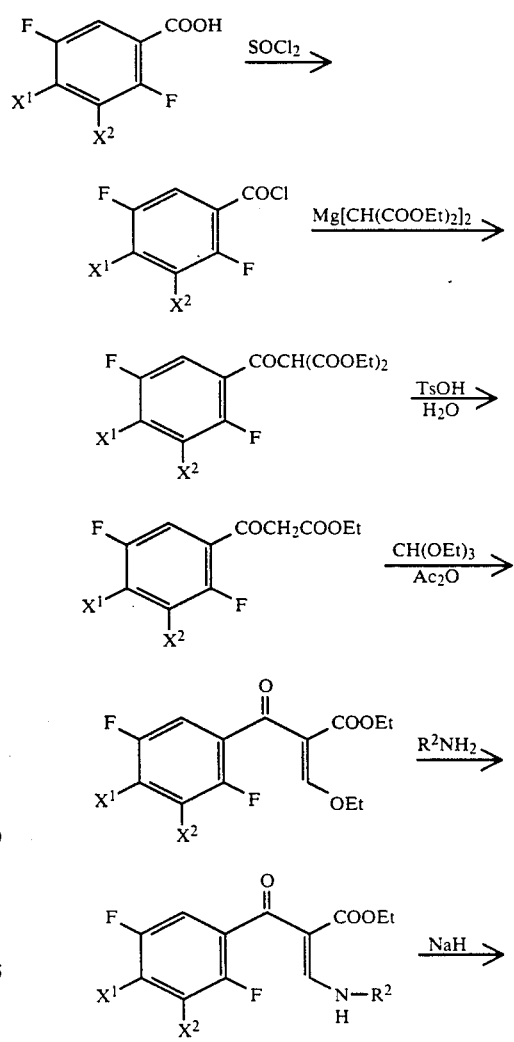

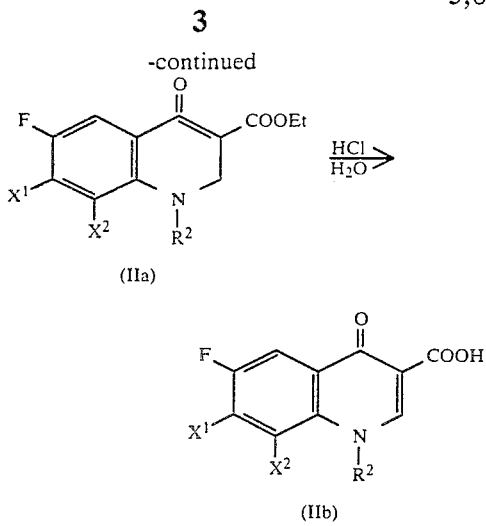

(IIa)

(IIb)

wherein $X^1$ and $X^2$ each is halogen, and $R^2$ has the same meaning as defined above.

The reactant (III) can be prepared, for example, as described in Reference Example.

The compound (I) of this invention can be prepared by reacting the starting material (II) with the reactant (III). This reaction can be performed in a solvent such as water, methanol, ethanol, acetonitrile, dimethyl sulfoxide (DMSO) or dimethylformamide (DMF). The reaction is performed at a temperature between 15°-200° C., preferably between 60°-120° C. or around the boiling point of the solvent for one to several hours, preferably in the presence of a base such as DBU (1,8-diazabicyclo[5,4,0]undec-7-ene), triethylamine, pyridine, or the like.

The compounds of the formula (I) can be converted into acid-addition salts thereof in a conventional manner, if deseired. The salt-forming acid illustratively includes an inorganic acid such as hydrochloric acid, sulfuric acid or phosphoric acid and an organic acid such as methanesulfonic acid, lactic acid, oxalic acid or acetic acid.

The compounds of this invention may also be led to salts with alkali metal such as sodium or potassium, or alkaline earth metal such as calcium.

Illustration examples of the compounds (I) are shown below.

(1) 1-Cyclopropyl-6,8-difluoro-7-(3-amino-4-methylenepyrrolidin-1-yl)-1,4-dihydro-4-oxo-3-quinolinecarboxylic acid.

(2) 1-Cyclopropyl-8-chloro-6-fluoro-7-(3-amino-4-methylenepyrrolidin-1-yl)-1,4-dihydro-4-oxo-3-quinolinecarboxylic acid.

(3) 1-Cyclopropyl-5-amino-6,8-difluoro-7-(3-amino-4-methylenepyrrolidin-1-yl)-1,4-dihydro-4-oxo-3-quinolinecarboxylic acid.

(4) 1-Cyclopropyl-6,8-difluoro-7-(3-methylamino-4-methylenepyrrolidin-1-yl)-1,4-dihydro-4-oxo-3-quinolinecarboxylic acid.

(5) 1-Cyclopropyl-6-fluoro-7-(3-amino-4-methylenepyrrolidin-1-yl)-1,4-dihydro-4-oxo-1,8-naphthyridine-3-carboxylic acid.

The compounds (I) of this invention can be administered orally or parenterally to human or animals. They can be formulated into tablets, capsules, pills, granules, injections, suppositories, and syrups together with pharmaceutically acceptable carriers, diluents, and/or fillers by a conventional pharmaceutical practice. Such carriers, diluents, and fillers illustratively include lactose, cane sugar, wheat starch, potato starch, magnesium stearate, gelatin, methyl cellulose, agar, water, etc. Stabilizers, emulsifiers, wet extenders, buffers, and other auxiliaries may be added thereto, if necessary. Suitable daily dosage for an adult is 10-2000 mg, preferably 300-600 mg through oral route, and 5-1500 mg, preferably 50-300 mg through parenteral route in a single or divided doses.

The following examples, reference examples and formulation are shown to clarify the practical embodiments of this invention.

The abbreviations used in the examples and reference examples shall have the following meanings:

Me: methyl
Et: ethyl
Bu: butyl
Ph: phenyl
MeOH: methanol
THF: tetrahydrofuran
DMF: dimethylformamide
DMSO: dimethyl sulfoxide
DBU: 1,8-diazabicyclo[5,4,0]undec-7-ene

EXAMPLE 1

1-Cyclopropyl-6,8-difluoro-7-(3-amino-4-methylenepyrrolidin-1-yl)-1,4-dihydro-4-oxo-3-quinolinecarboxylic acid (I—1)

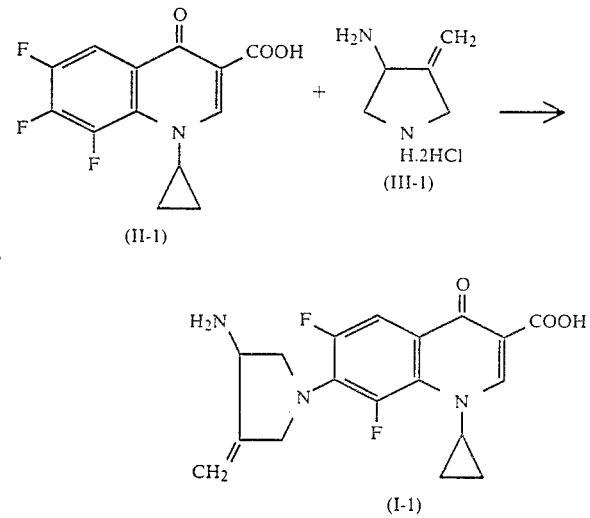

A solution of 400 mg (1.41 mM) of 1-cyclopropyl-6,7,8-trifluoro-1,4-dihydro-4-oxo-3-quinolinecarboxylic acid (II—1), 481 mg (2.81 mM) of 3-amino-4-methylene-1-pyrrolidine dihydrochloride, and 913 mg (6 mM) of DBU in 20 ml of dry acetonitrile is refluxed for 1.5 hours. After cooling, the reaction mixture is neutralized with acetic acid. The resulting crystals are collected by filtration, washed with acetonitrile, and dried to give 428 mg (Yield: 84%) of the objective compound (I—1).

mp.: 225°-231° C. (dec.): Anal. Calcd. (%) for $C_{18}H_{17}N_3O_3F_2$: : C, 59.83; H, 4.75; N, 11.63; F, 10.52: Found (%): C, 59.73; H, 4.88; N, 11.78; F, 10.36.

$^1$HNMR ($d_6$-DMSO) δ:
1.1-1.4 (m, 4H); 3.7-4.2 (m, 2H); 4.2-4.35 (m, 1H); 4.45-4.6 (m, 1H); 5.1 (bs, 1H); 5.2 (bs, 1H); 7.73 (dd, 2 Hz, 14 Hz); 8.64 (s, 1H) IR (Nujol): 1710, 1620, 1540, 1510 cm$^{-1}$.

EXAMPLE 2

1-Cyclopropyl-8-chloro-6-fluoro-7-(3-amino-4-methylenepyrrolidin-1-yl)-1,4-dihydro-4-oxo-3-quinolinecarboxylic acid (I−2)

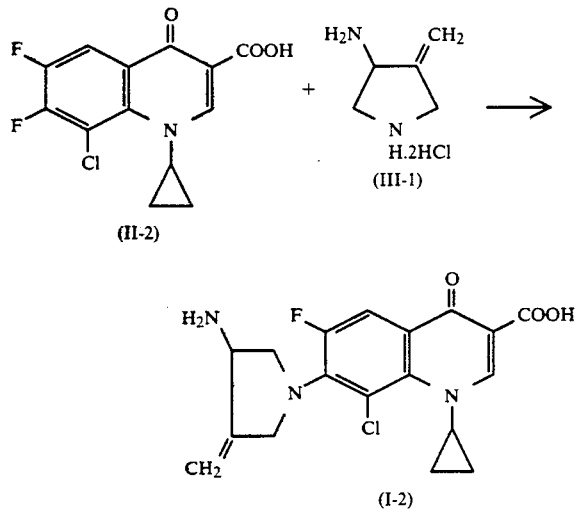

A solution of 175 mg (0.585 mM) of 1-cyclopropyl-8-chloro-6,7-difluoro-1,4-dihydro-4-oxo-3-quinolinecarboxylic acid (II−2), 200 mg (1.17 mM) of 3-amino-4-methylene-1-pyrrolidine dihydrochloride (III−1), and 356 mg (2.34 mM) of DBU in 10 ml of dry acetonitrile is refluxed for 1.5 hours. The reaction mixture is cooled at room temperature, neutralized with acetic acid and concentrated under reduced pressure. The residue is dissolved in methylene chloride, and the solution is washed with water, dried over $MgSO_4$ and concentrated under reduced pressure. The residue is crystallized from methanol-methylene chloride and treated with methanol to give 145 mg (Yield: 66%) of the objective compound (I−2).

mp. 182°-187° C. (dec.)

Anal Calcd. (%) for $C_{18}H_{17}N_3O_3FCl.0.7H_2O$: : C, 55.38; H, 4.75; N, 10.76; F, 4.87:

Found (%): C, 55.21; H, 4.63; N, 10.31; F, 4.84.

$^1$HNMR ($d_6$-DMSO) δ:

0.8-1.3 (m, 4H); 3.0-4.6 (m, 6H); 5.1 (bs, 1H); 5.2 (bs, 1H); 7.87:

(d, 1H, 13 Hz); 8.8 (s, 1H):

IR (Nujol): 1710, 1610, 1570 cm$^{-1}$.

EXAMPLE 3

1-Cyclopropyl-5-amino-6,8-difluoro-7-(3-amino-4-methylenepyrrolydin-1-yl)-1,4-dihydro-4-oxo-3-quinolinecarboxylic acid (I−3)

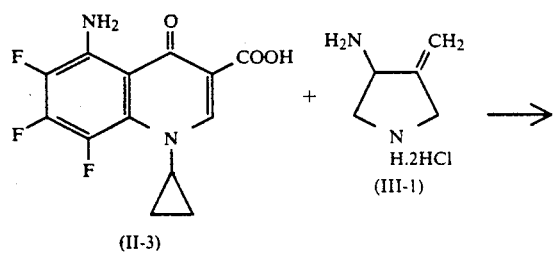

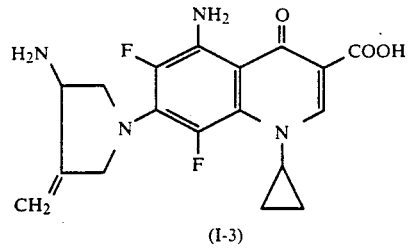

A solution of 174 mg (0.583 mM) of 1-cyclopropyl-5-amino-6,7,8-trifluoro-1,4-dihydro-4-oxo-3-quinolinecarboxylic acid (II−3), 200 mg (1.17 mM) of 3-amino-4-methylene-1-pyrrolidine dihydrochloride (III−1), and 356 mg (2.34 mM) in 10 ml of dry acetonitrile is refluxed for 5 hours. The reaction mixture is cooled at room temperature and neutralized with acetic acid. The resulting crystals are collected by filtration and treated with methanol to give 163 mg (Yield: 74.3%) of crude product. It is recrystallized from methanol-acetonitrile to give 117 mg of the objective compound (I−3). mp. 202°-209° C. (dec.)

Anal Calcd. (%) for $C_{18}H_{18}N_4O_3F_2.0.25H_2O$: : C, 56.76; H, 4.90; N, 14.71; F, 9.98:

Found (%): C, 56.77; H, 4.72; N, 14.47; F, 10.05:

$^1$HNMR ($d_6$-DMSO) δ:

0.95-1.25 (m, 4H); 3.0-4.6 (m, 6H); 5.08 (bs, 1H); 5.17 (bs, 1H);

7.18 (bs, 2H); 8.48 (s, 1H):

IR (Nujol): 1710, 1630, 1580, 1510 cm$^{-1}$.

EXAMPLE 4

1-Cyclopropyl-6-fluoro-7-(3-amino-4-methylenepyrrolidin-1-yl)-1,4-dihydro-4-oxo-1,8-naphthyridine-3-carboxylic acid (I−4)

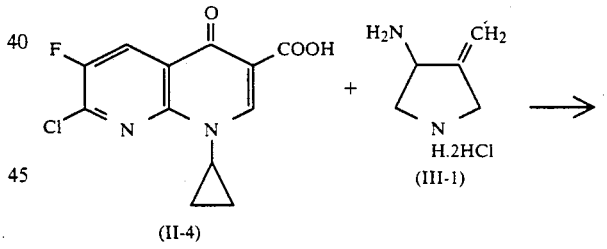

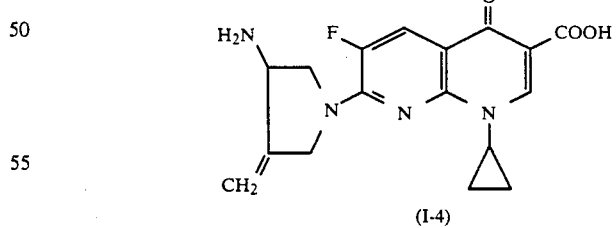

A solution of 165 mg (0.584 mM) of 1-cyclopropyl-7-chloro-6-fluoro-1,4-dihydro-4-oxo-1,8-naphthyridine-3-carboxylic acid (II−4), 200 mg (1.17 mM) of 3-amino-4-methylene-1-pyrrolidine dihydrochloride (III−1), and 445 mg (3 mM) of DBU in 10 ml of dry acetonitrile is heated on oil bath at about 100° C. for 5 minutes. The reaction mixture is cooled at room temperature, and the resulting crystals are collected by filtration and treated with acetonitrile to give 171 mg (Yield: 85%) of crude product. It is recrystallized from methanol-acetonitrileaqueous ammonia to give 122 mg of the objective compound (I−4). mp. 244°–252° C. (dec.)

Anal Calcd. (%) for $C_{17}H_{17}N_4O_3F$: C, 59.30; H, 4.98; N, 16.27; F, 5.52:

Found (%): C, 59.57; H, 5.17; N, 16.31; F, 5.55.

$^1$HNMR (d$_6$-DMSO) δ:

1.0–1.3 (m, 4H); 3.6–4.3 (m, 4H); 4.49 (bs, 2H); 5.17 (bs, 1H);

5.25 (bs, 1H); 7.99 (d, 1H, 13 Hz); 8.58 (s, 1H):

IR (Nujol): 1710, 1620, 1590, 1550 cm$^{-1}$.

EXAMPLE 5

1-Cyclopropyl-6,8-difluoro-7-(3-methylamino-4-methylenepyrrolidin-1-yl)-1,4-dihydro-4-oxo-3-quinolinecarboxylic acid (I−5)

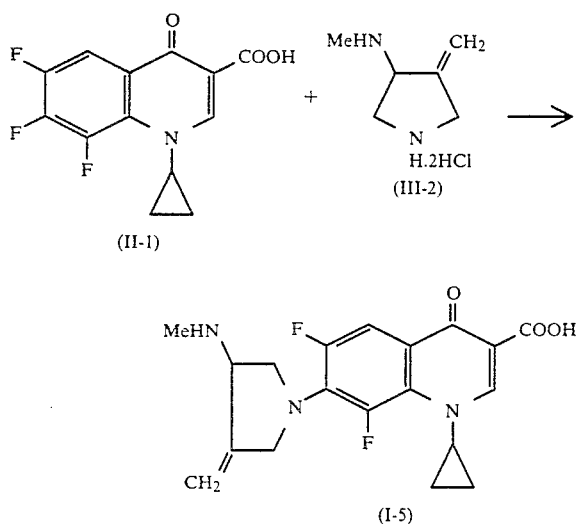

A solution of 350 mg (1.24 mmol) of 1-cyclopropyl-6,7,8-trifluoro-1,4-dihydro-4-oxo-3-quinolinecarboxylic acid (II−1), 424 mg (2.48 mmol) of 3-methylamino-4-methylene-1-pyrrolidine dihydrochloride, and 754 mg of DBU in 15 ml of acetonitrile is refluxed for 2 hours. After cooling, the reaction mixture is neutralized with acetic acid. The resulting crystals are collected by filtration, washed with acetonitrile, and dried to give 368 mg (Yield: 82%) of the objective compound (I−5). mp. 239°–243° C.

$^1$HNMR (CDCl$_3$) δ:

1.14–1.19 (4H, m); 2.32 (3H, s); 3.48–3.60 (2H, m); 3.93–4.18 (2H, m); 4.22–4.48 (2H, m); 5.13 (2H, bs); 7.74 (1H, dd, J=2, 14 Hz); 8.63 (1H, s).

REFERENCE EXAMPLE

3-Amino-4-methylene-1-pyrrolidine Dihydrochloride (II−1)

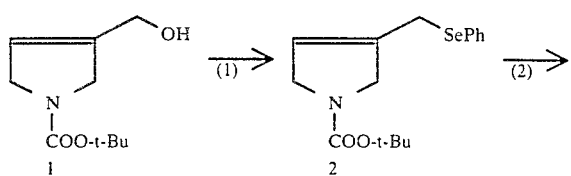

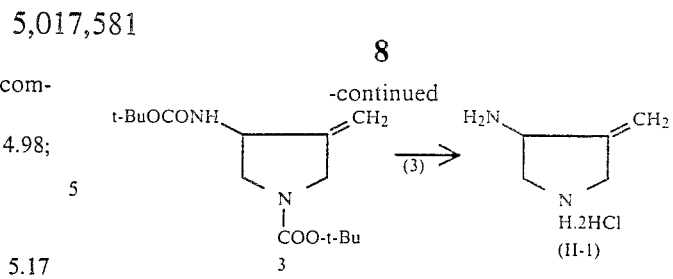

(1) To a solution of 1.9 g (9.54 mM) of the alcohol 1 in 50 ml of dry methylene chloride are added 2.31 g (11.45 mM) of tri-n-butylphosphine and 3.2 g (10.5 mM) of N-(phenylseleno)phthalimide under stirring at −70° C., and subsequently the reaction mixture is stirred at the same temperature for 40 minutes. The resulting precipitate is filtered off, and the filtrate is concentrated. The residue is chromatographed on a column of silica gel, eluting with toluene-ethyl acetate (4:1 v/v) to give 2.95 g (Yield: 91.4%) of 1-(N-tert-butoxycarbonyl)-3-phenylselenomethyl-3-pyrroline 2.

$^1$HNMR (CDCl$_3$) δ:

1.46 (s, 9H); 3.55 (bs, 2H); 3.9–4.3 (m, 4H); 5.35 (bs, 1H); 7.2–7.6 (m, 5H)

(2) To a solution of 2.7 g (7.98 mM) of phenylseleno compound 2 in 30 ml of dry methanol are added 2.3 g (20 mM) of tert-butyl carbamate, 4 g (40 mM) of Et$_3$N, and 2.66 g (20 mM) of N-chlorosuccinimide in order at −25° C. under stirring, and the mixture is stirred at −25° C. to −15° C. for 40 minutes. The reaction mixture is concentrated, and the resulting residue is washed with ethyl acetate, d-HCl, and water. The solution is dried over MgSO$_4$ and concentrated. The residue is chromatographed on a column of silica gel, eluting with n-hexane-ethyl acetate (4:1 v/v) to give 2.25 g (Yield: 95%) of 1-(N-tert-butoxycarbonyl)-3-tertbutoxycarbonylamino-4-methylene-3-pyrrolidine 3.

$^1$HNMR (CDCl$_3$) δ:

1.46 (s, 9H); 1.47 (s, 9H); 2.9–3.2 (m, 1H); 3.8–4.2 (m, 4H);

4.5–4.8 (m, 2H); 5.05–5.3 (m, 2H).

(3) To a solution of 952 mg (3.19 mM) of methylene compound in 10 ml of dry methylene chloride is added 10 ml of 3M-HCl/MeOH under ice-cooling, and the reaction mixture is stirred at room temperature for 2 hours. The resulting crystals are collected by filtration and washed with 3 ml of methylene chloride-methanol (2/1 v/v) twice and dried to give 502 mg (Yield: 92%) of the objective 3-amino-4-methylene-1-pyrrolidine dihydrochloride (III−1). mp. 228°–232° C. (dec.)

$^1$HNMR (D$_2$O) δ:

3.59 (dd, J=13 Hz, 6.3 Hz, 1H); 3.99 (dd, J=13 Hz, 8 Hz, 1H); 4.1–4.24 (m, 2H); 4.56–4.69 (m, 1H); 5.63–5.73 (m, 2H).

EFFECT OF THE INVENTION

Experiment (Antibacterial spectrum)

The antibacterial activity was determined by measuring minimum growth inhibitory concentrations (MICs) in accordance with the method as designated by the Japan Society of Chemotherapy. The results are shown in Table 1.

A, B, C, and D in the table indicate the following meanings:

A: *Staphylococcus aureus* Smith
B: *Staphylococcus aureus* SR 14 (R)
C: *Escherichia coli* 7437
D: *Escherichia coli* PC 51149 B The test microorganisms were used at $10^6$ cells/ml.

| Compound No. | MICs (µg/ml) | | | |
|---|---|---|---|---|
| | A | B | C | D |
| I-1 | 0.05 | 0.05 | <0.003 | <0.003 |
| I-2 | 0.01 | 0.02 | <0.003 | <0.003 |
| I-3 | 0.02 | 0.05 | <0.003 | <0.003 |
| I-4 | 0.1 | 0.1 | <0.003 | 0.006 |
| I-5 | 0.05 | 0.05 | <0.003 | 0.006 |

These results have proven that the compounds of this invention show strong antibacterial activities against Gram-positive and Gram-negative bacteria.

Moreover, neither convulsion nor psychotropic action was observed in mice, when Compound I—1 was orally administered to the mice at a dose of 10 mg.

Formulation (per capsule)

| | |
|---|---|
| 1-Cyclopropyl-6,8-difluoro-7-(3-methylamino-4-methylene-pyrrolidin-1-yl)-1,4-dihydro-4-oxo-3-quinolinecarboxylic acid (I-5) | 25 mg |
| Lactose | 100 mg |
| Wheat Starch | 15 mg |
| Gelatin | 5 mg |
| Magnesium stearate | 5 mg |
| Total | 10 mg |

What we claim is:

1. A compound of the formula:

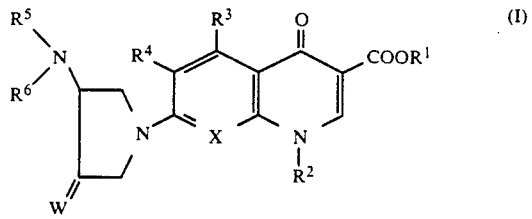

wherein $R^1$ is hydrogen or a protecting group; $R^2$ is $C_1$-$C_3$ alkyl or $C_3$-$C_7$ cycloalkyl; $R^3$ is hydrogen, hydroxy, or amino; $R^4$ is halogen; $R^5$ and $R^6$ each is identically or differently hydrogen or $C_1$-$C_3$ alkyl; W is $C_1$-$C_3$ alkylidene; X is N or C-Y; Y is hydrogen or halogen; or a pharmaceutically acceptable salt thereof.

2. The compound claimed in claim 1, wherein X is C-Y, and Y is halogen.

3. The compound claimed in claim 2, namely 1-cyclopropyl-6,8-difluoro-7-(3-amino-4-methylenepyrrolidin-1-yl)-1,4-dihydro-4-oxo-3-quinolinecarboxylic acid.

4. The compound claimed in claim 2, namely 1-cyclopropyl-8-chloro-6-fluoro-7-(3-amino-4-methylenepyrrolidin-1-yl)-1,4-dihydro-4-oxo-3-quinolinecarboxylic acid.

5. The compound claimed in claim 2, namely 1-cyclopropyl-5-amino-6,8-difluoro-7-(3-amino-4-methylenepyrrolidin-1-yl)-1,4-dihydro-4-oxo-3-quinolinecarboxylic acid.

6. The compound claimed in claim 2, namely 1-cyclopropyl-6,8-difluoro-7-(3-methylamino-4-methylenepyrrolidin-1-yl)-1,4-dihydro-4-oxo-3-quinolinecarboxylic acid.

7. The compound claimed in claim 1, wherein X is N.

8. The compound claimed in claim 7, namely 1-cyclopropyl-6-fluoro-7-(3-amino-4-methylenepyrrolidin-1-yl)-1,4-dihydro-4-oxo-1,8-naphthyridine-3-carboxylic acid.

9. An antibacterial composition comprising a pharmacologically effective amount of the compound claimed in claim 1 as an active ingredient and a pharmaceutically acceptable carrier.

* * * * *